US008361776B2

(12) United States Patent
Patel et al.

(10) Patent No.: US 8,361,776 B2
(45) Date of Patent: Jan. 29, 2013

(54) ADAPTATION OF PITMAN MOORE STRAIN OF RABIES VIRUS TO PRIMARY CHICK EMBRYO FIBROBLAST CELL CULTURES

(75) Inventors: Pradip Maganlal Patel, Gujarat (IN); Pankaj Ramanbhai Patel, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 169 days.

(21) Appl. No.: 12/667,090

(22) PCT Filed: Apr. 24, 2008

(86) PCT No.: PCT/IN2008/000262
§ 371 (c)(1), (2), (4) Date: Mar. 24, 2010

(87) PCT Pub. No.: WO2009/004641
PCT Pub. Date: Jan. 8, 2009

(65) Prior Publication Data

US 2010/0189746 A1 Jul. 29, 2010

(30) Foreign Application Priority Data

Jul. 3, 2007 (IN) ......................... 1275/MUM/2007

(51) Int. Cl.
*C12N 7/00* (2006.01)
*C12N 5/073* (2010.01)

(52) U.S. Cl. ..................................... 435/235.1; 435/363

(58) Field of Classification Search ........................ None
See application file for complete search history.

(56) References Cited

U.S. PATENT DOCUMENTS 4,115,195 A * 9/1978 Barth et al. ................... 435/237

OTHER PUBLICATIONS

Gluck et al. Neurochemical Pathology (1986), 4(2), 69-75.*
Rabies Vaccine INOVAX, RABIES, Manufactured by Sanofi Pasteur SA, Lyon France, Dec. 2005.*
Laboratory techniques in rabies, Fourth edition, Apr. 1996, Table of Contents, pp. i-ix.
Nicholson, Cell culture vaccines for human use: general considerations, chapter 24, Laboratory techniques in rabies, Fourth edition, Apr. 1996, pp. 271-279.
Montagnon, Purified Vero Cell Vaccine for Humans, chapter 26, Laboratory techniques in rabies. Fourth edition, Apr. 1996, pp. 285-289.
N.Veeraraghavan, The Value of Duck -embryo Vaccine and High-Egg-Passage Flury Vaccine in Experimental Rabies Infection in Guinea -Pigs, 1963,29, pp. 323-330.
P. Reculard, Cell culture vaccine for veterinary use, chapter 32, Laboratory techniques in rabies. Fourth edition, Apr. 1996, pp. 314-323.
Patrice Coulon et al, Invasion of the Peripheral Nervous System of Adult Mice by the CVS Strain of Rabies Virus and its Avirulent Derivative AvO1. Journal of Virology, Aug. 1989, pp. 3550-3554.
A. King, Cell culture of Rabies virus, chapter 10, Laboratory techniques in rabies. Fourth edition, Apr. 1996, pp. 114-129.
Tordo, Characteristics and molecular biology of the rabies virus, chapter 3, Laboratory techniques in rabies. Fourth edition, Apr. 1996, pp. 28-51.
B. Kissi et ai, Dynamics of rabies virus quasispecies during serial passages in hetrologous hosts, Journal of General Virology, 1999, 80, pp. 2041-2050.
W.A. Webster et al., virus isolation in neuroblastoma cell culture, chapter 8, Laboratory techniques in rabies. Fourth edition, Apr. 1996, pp. 96-104.
R. Gluck, Purified duck embryo vaccine, chapter 22, page No. 253, Laboratory techniques in rabies.Fourth edition WHO 1996.
XianfuWu et al., From brain passage to cell adaptation: the road of human rabies vaccine development,Expert Rev, Vaccines 10(11),1597-1608(2011).
M. Majer et al., A comparison of the Pasteur and Pitman Moore strains of the rabies virus for the production of rabies vaccine in human diploid cells,page No. 249-256, Journal of Biological Standardization 1977, vol. 5.
N. Veeraraghavan, The value of duck embryo vaccine and high egg passage Fury vaccine in Expermental Rabies infection in Guinea -Pigs, 1963, 29, 323-330.

* cited by examiner

*Primary Examiner* — Bao Li
(74) *Attorney, Agent, or Firm* — Ladas & Parry LLP

(57) ABSTRACT

The present invention relates to a process of adaptation of Pitman Moore strain of rabies virus to Primary chick fibroblast cells for the production of rabies vaccine.

9 Claims, 6 Drawing Sheets

ADAPTATION OF PITMAN MOORE STRAIN OF RABIES VIRUS TO PRIMARY CHICK EMBRYO FIBROBLAST CELL CULTURES

FIELD OF INVENTION

The present invention relates to the field of vaccine, in particular, the adaptation of Pitman Moore rabies virus strain (PM strain) into Purified Chick Embryo Fibroblast Cell culture for producing an improved and highly purified vaccine. Specifically the adapted PM rabies virus strain gives a high virus titer, which in turn gives high yields in terms of vaccine doses per egg and is also highly immunogenic.

BACKGROUND AND PRIOR ART OF THE INVENTION

Rabies is a zoonotic viral disease which infects domestic and wild animals. Once symptoms of the disease develop, rabies is fatal to both animals and humans. However, when individuals are vaccinated with a rabies vaccine either prior to the virus exposure or after the exposure when combined with thorough cleaning of the wound with antiseptic and anti-rabies antibodies, the individuals are generally well protected. Human rabies vaccines are made from inactivated or attenuated rabies virus and have gone through successive improvements since the time of Pasteur. The first rabies vaccine was developed by Pasteur which was nerve tissue based and virus was inactivated by drying but this vaccine had a risk of activation of the virus and allergic reaction due to the presence of nerve tissue or myelin. Myelin free vaccines prepared from neonatal mouse brains were introduced by Fuenzalida et. al. (*Vaccines: Fourth edition*, chapter 37, Plotkin, Rupprecht and Koprowski).

Subsequently, Duck Embryo Vaccine (DEV) for rabies was developed. DEV for rabies was prepared from virus propagated in embryonated duck eggs. It was less immunogenic than the brain tissue vaccine. Fourteen to twenty three daily inoculations were recommended for DEV and sometime such high dosages also did not protect against rabies after severe exposure. (*Vaccines: Fourth edition*, chapter 37, Page number 1018, Plotkin, Rupprecht and Koprowski). The other drawback associated with DEV was that it also had myelin based proteins, which caused side reactions so later on it was banned by the World Health Organization (WHO). Thus there was a long need for highly immunogenic rabies vaccine that could be used safely and effectively at low doses, both for primary immunization and for treatment after exposure. These vaccines would also greatly reduce the number and severity of post vaccinal reactions.

Such a need was satisfied by the development of tissue/cell culture vaccines. The cell culture vaccine is not only safer compared to the former brain tissue vaccines by virtue of the absence of neuronal tissue but also is more efficacious. Several cell culture based vaccines have been developed in order to achieve high immunogenicity and safety like Purified Duck Embryo Vaccine (PDEV), 1$^{st}$ generation vaccines like Human Diploid Cell Vaccine (Wiktor et al., 1964. *J. Immunol.* 93:353-366) and 2$^{nd}$ generation vaccines like Purified Chick Embryo Cell Vaccine (PCECV), Purified Vero Cell Rabies Vaccine, Rabies Vaccine Adsorbed (RVA), and Primary Hamster Kidney Cell Vaccine (PHKCV) etc. (Ref: *JIACM* 2006; 7(1): 39-46).

The technical advancement leading to the development of the above vaccines included the adaptation of Pitman Moore strain of rabies virus to continuous cell lines such as Vero cells (e.g. Purified Vero Cell Rabies Vaccine—Abhayrab™ & Verorab™) and MRC-5 human diploid cell culture line [e.g. Human Diploid Cell Vaccine (HDCV)—MIRV-HDC in India] [Ref: JIACM 2006; 7(1): 39-46] or in Duck Embryos in situ (e.g. Purified Duck Embryo Vaccine-PDEV—Lyssavac N) (Ref: *Laboratory Techniques in Rabies; Fourth Edition*, Edi. by F. X. Meslin, M M Kaplan & H Koprowski, WHO Geneva-1996).

Both Vero and MRC-5 cell lines are continuous cell lines, and hence necessitate the testing of cellular residual DNA in the finished product (Ref. European Pharmacopoeia, 2004) which may be due to risk of either transmission of latent viruses & other agents. Moreover, the yields obtained with Vero cells are substantially low even when PM strain is used for preparing the vaccine. PDEV is a suspension vaccine and hence this vaccine does not qualify for Intra-dermal (ID) application. Moreover, the technology suffers from attaining low yields (1.8-2.2 doses/egg). The process time is also of 88 days which is too long. The commercially available PDEV vaccine uses a preservative thiomersal, which has been linked to possible Autism in young children (ncirs usyd edu au/facts/f thiomersal) Additionally, the process for production of PDEV is long, cumbersome and not preferred for large scale production because it gives low yield. HDCV is considered gold standards vaccine but it is highly expensive. Therefore, there is a need to provide an improved and highly immunogenic rabies vaccine which provides better yield as well as is less expensive using cell culture based technology.

U.S. Pat. No. 4,115,195 (Rudolph Barth et al.) describes a process to manufacture rabies vaccine. It teaches that Chick Embryo Fibroblast cells, along with other cultures of cell strains can be used to make rabies vaccine with various viruses like viruses of strain VP 11, strain Pasteur, PM strain, or homogenized Chick-Embryo material containing viruses of strain Flury LEP (Low egg passage) or Flury HEP (High egg passage). The patent also specifically provides examples for use of rabies virus fixed strain VP 11, Flury HEP and Flury LEP to infect Chick Embryo Fibroblast cells. However, this document does not teach the adaptation of Pitman Moore strain (Wistar strain PM-HDCS, 1503-3M) either to Primary Duck Embryo Fibroblast Cells or to Primary Chick Embryo Fibroblast cells. Also, the media used in the present invention is a unique combination medium, which is not taught in U.S. Pat. No. 4,115,195, and is exclusively designed for PM rabies virus to infect Primary Chick Embryo Fibroblast Cells.

The present inventors have surprisingly found that the Pitman Moore strain could be adapted to Primary chick fibroblast cell culture. Such adaptation has provides a method of preparing the rabies vaccine in large quantities, having excellent yield, with low throughput time and easily scalable. The vaccine produced will be suitable for Intra Dermal application in addition to intramuscular (IM) application, since the vaccine is not a suspension.

According to the present invention, the rabies vaccine prepared by adaptation of Pitman Moore to primary chick fibroblast cell culture is more advantageous than many other continuous cell lines based rabies vaccine and is more readily scalable to large scale commercial vaccine production. The vaccine produced by the present process has a very high yield, efficacy, safety as well as the process is much cost effective than many of the other processes known for preparation of rabies vaccine, preferably when the process is carried out using Polyethylene Terephthalate (PET) Tissue Culture treated (TC) Roller bottles.

The present inventors have surprisingly found that Pitman Moore virus can be severely infected in Primary chick fibroblast cell culture with unique combination medium as described elsewhere, under suitable process conditions as hereinafter described in details, using PET TC Roller bottles. Such preferred embodiments provide vaccine with high yield, greater potency and immunogenicity which makes the vaccine comparatively cost effective.

OBJECT OF THE INVENTION

The primary objective of the present invention is the adaptation of the Pitman Moore rabies virus strain to Chick Embryo Fibroblast cell culture in order to obtain a rabies vaccine.

In an embodiment of present invention is provided a process for the production of an immunogenic and highly Purified Chick Embryo Cell Vaccine$^{PM}$ (henceforth called PCECV$^{PM}$) using Pitman Moore strain for active immunization against Rabies.

A further embodiment of the invention is to develop a high yielding unique process for obtaining the vaccine by a simpler process.

In a still further embodiment of the present invention is provided a suitable medium composition in order to achieve high infectivity of Pitman Moore strain rabies virus into Chick Embryo Fibroblast Cells.

SUMMARY OF THE INVENTION

The present invention provides a process for the adaptation of Pitman Moore rabies virus strain to Chick Embryo Fibroblast cell culture. The original Pitman Moore strain (Wistar strain PM-HDCS, 1503-3M) is first adapted to mice via one intracerebral passage and subsequently in duck eggs by repeated passages which the present inventors have further adapted to the duck embryo fibroblast cells by successive passages, followed by adaptation to Primary chick embryo fibroblast cells by further serial passages using suitable medium and other suitable culture parameters to obtain the rabies vaccine.

Another aspect of the present invention provides a unique combination medium in order to achieve high and severe infectivity of Pitman Moore rabies virus strain into Purified Chick Embryo Fibroblast Cells.

In another aspect of the invention is provided an inactivated Purified Chick Embryo Cell Rabies Vaccine using PM rabies virus Strain having high purity and immunogenicity.

DETAILED DESCRIPTION OF THE INVENTION

The present invention relates to the adaptation of Pitman Moore rabies virus strain in primary cultures of Chick/Duck fibroblast cells. The eggs used are SPF quality chicken eggs. SPF chicken eggs and Pitman Moore rabies virus strain are approved substrate and approved virus strain by WHO for the manufacturing of the rabies vaccine for humans. In a preferred embodiment, the PM rabies virus strain is adapted to chick fibroblast cells in roller cultures using PET TC roller bottles which gives higher yield compared to several other technologies.

Figure 1:
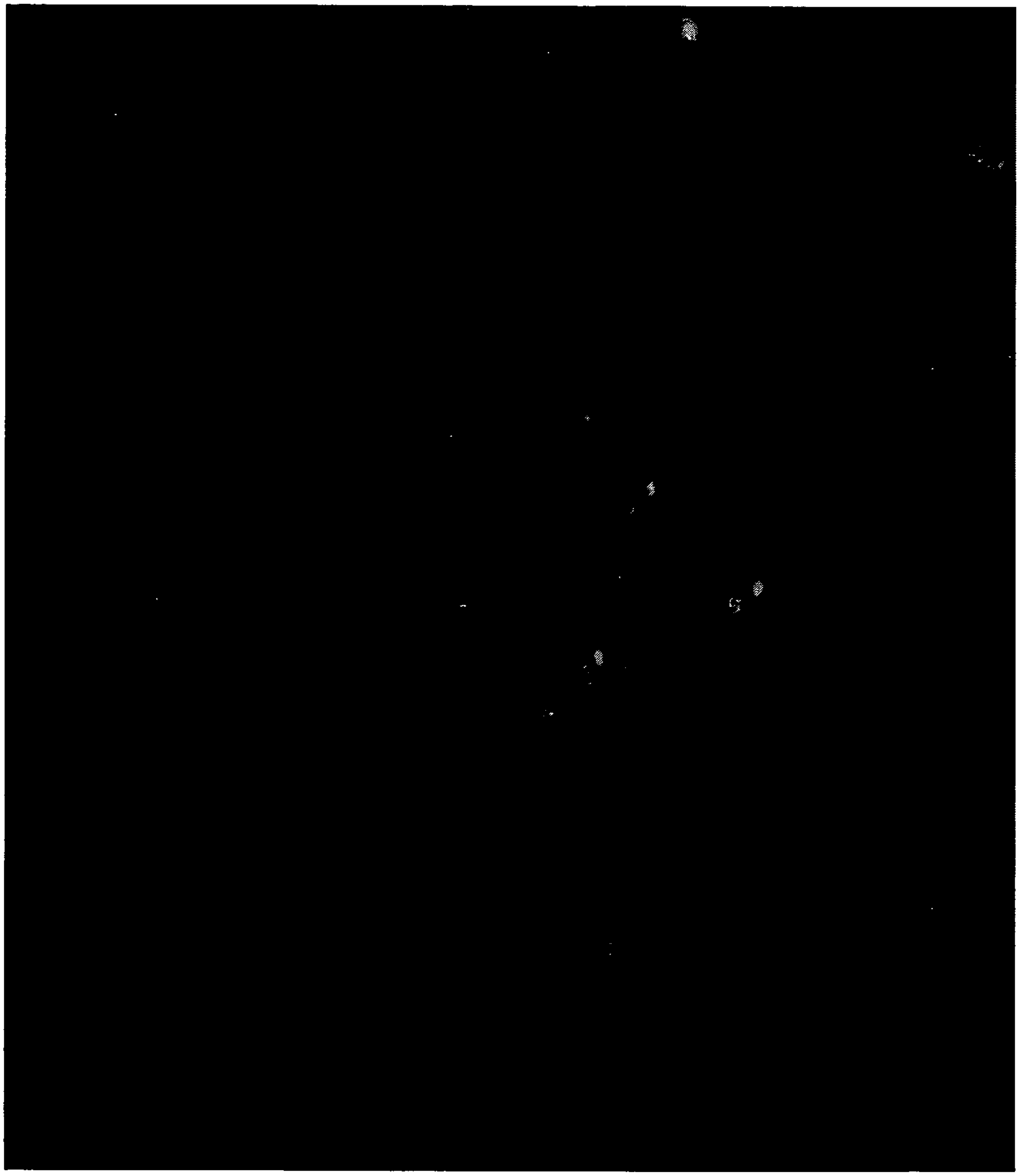
FIG. 1: Shows rabies specific fluorescence of 03PM/Duck/S.Pas.07 in duck culture on day 5$^{th}$
Figure 2:
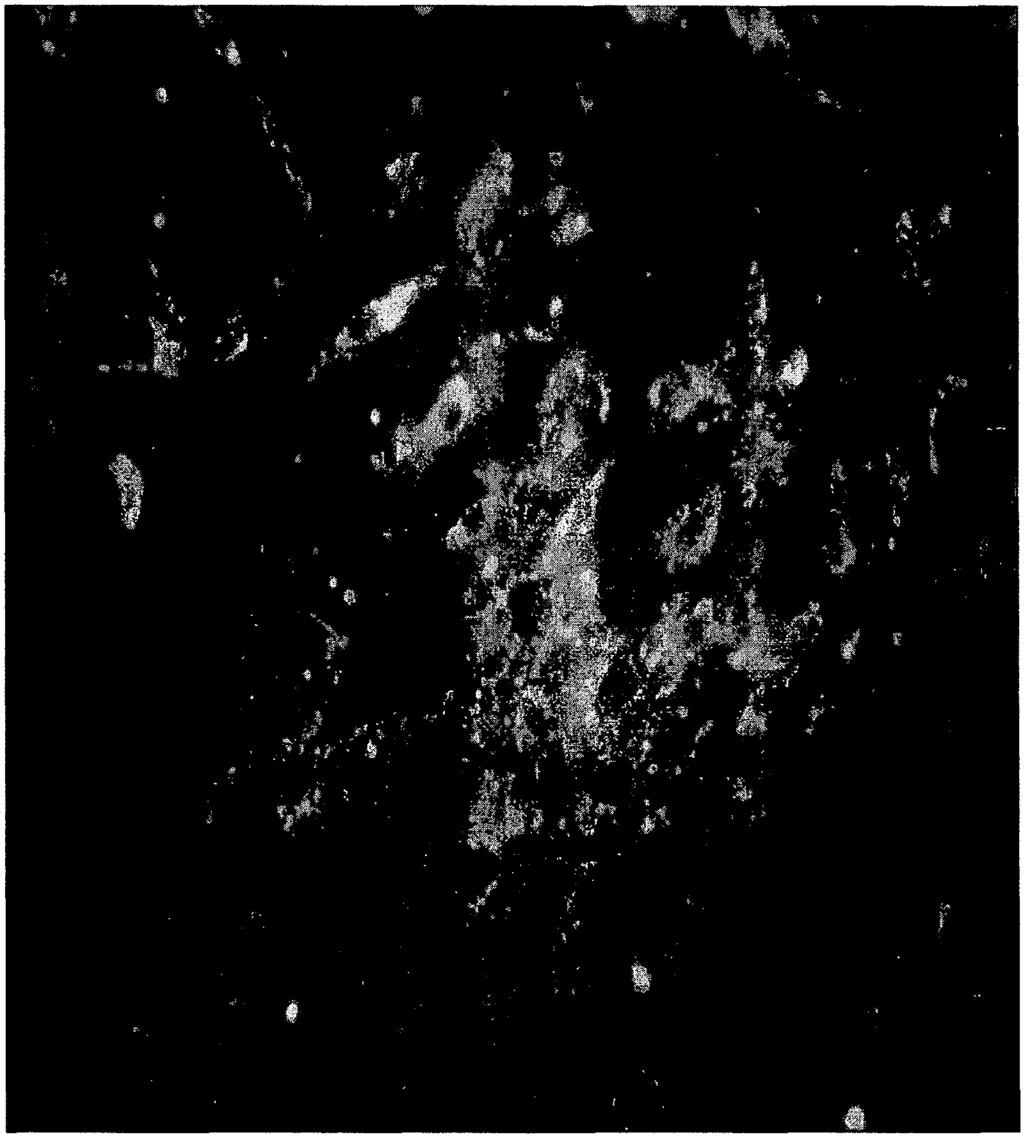
FIG. 2: Shows rabies specific fluorescence of 04PM/Chick/S.Pas.09 in Chick Embryo Culture (CEC) on day 5$^{th}$
Figure 3:
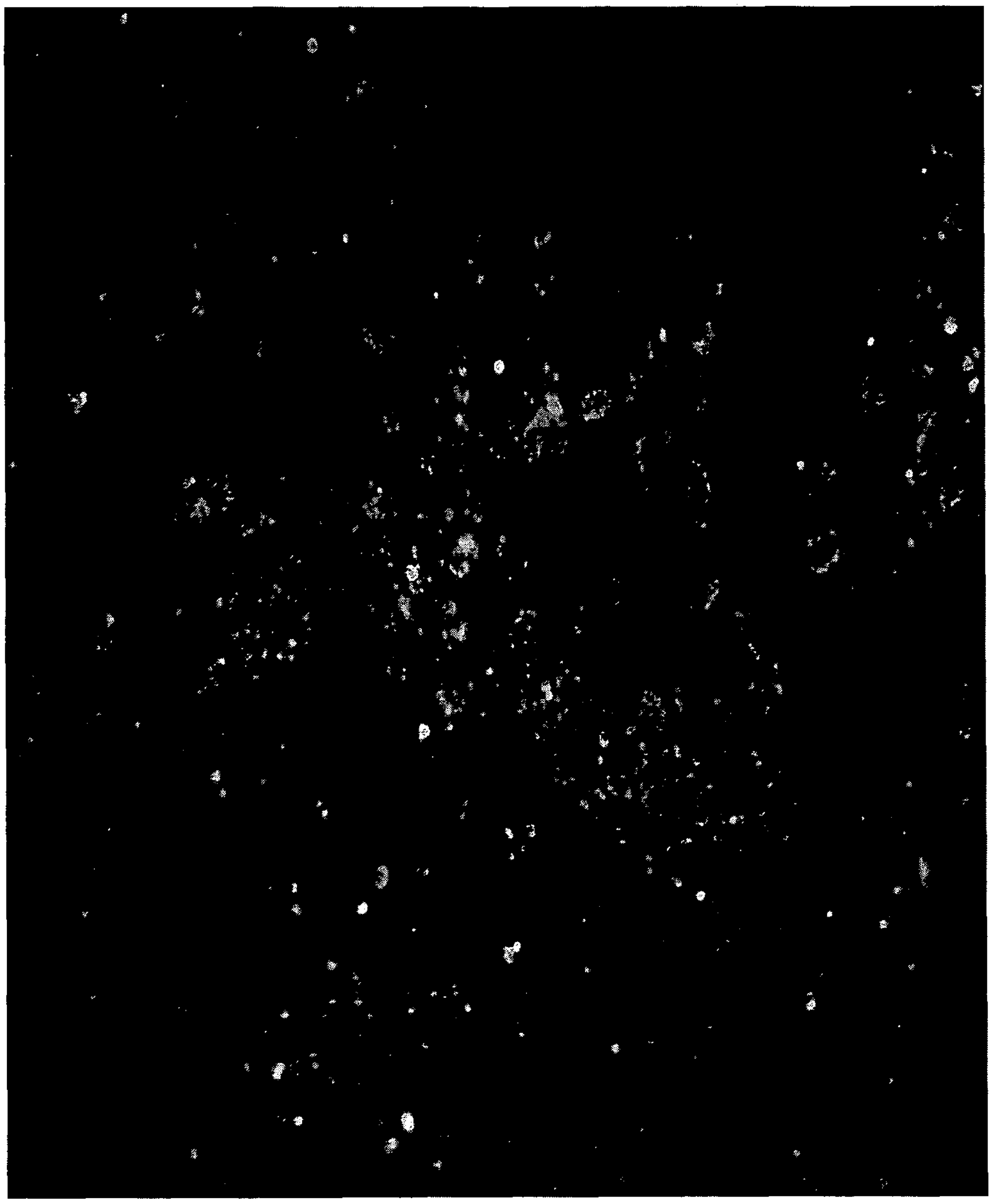
FIG. 3: Shows rabies specific fluorescence of 04PM/Chick/S.Pas.10 in Chick Embryo Culture (CEC) on day 3$^{rd}$
Figure 4:
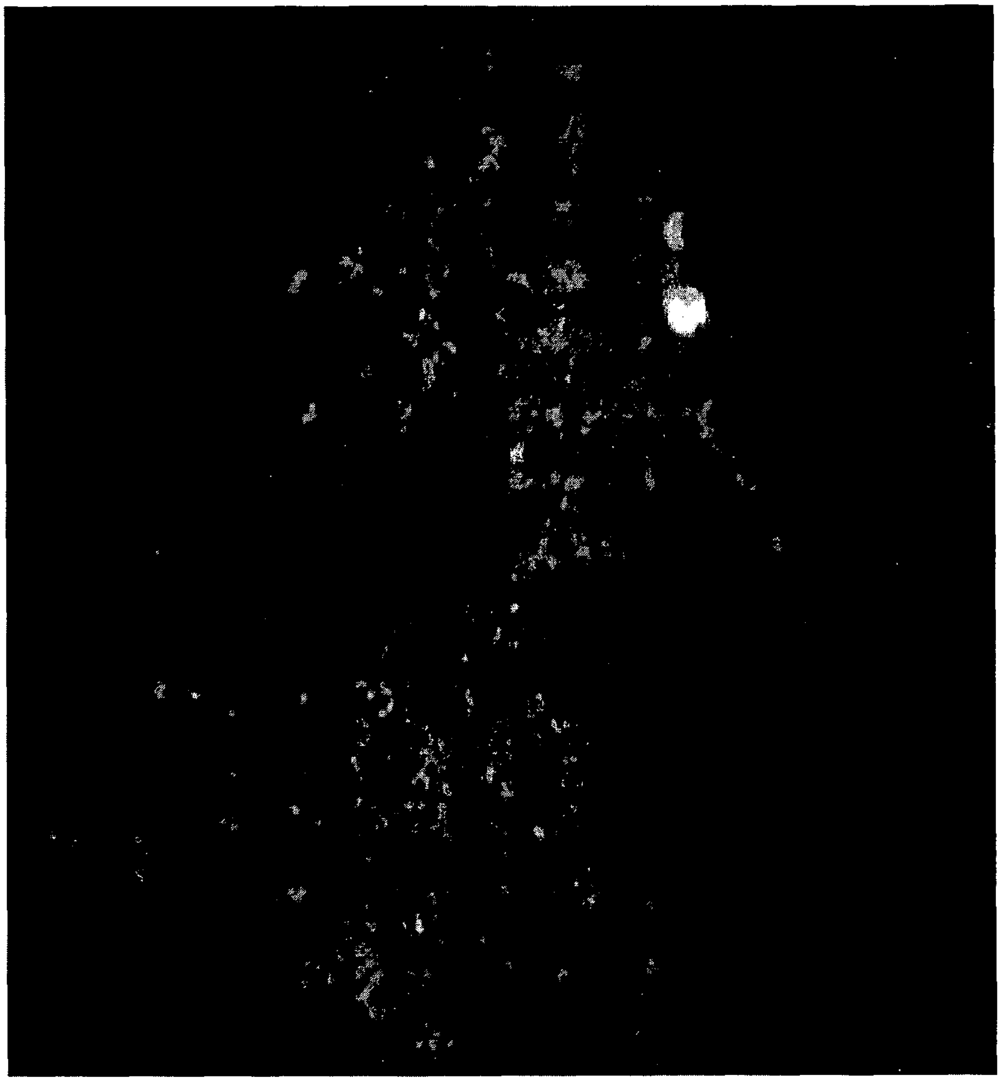
FIG. 4: Shows rabies specific fluorescence of 04PM/Chick/S.Pas.11 in Chick Embryo Culture (CEC) on day 3$^{rd}$
Figure 5:
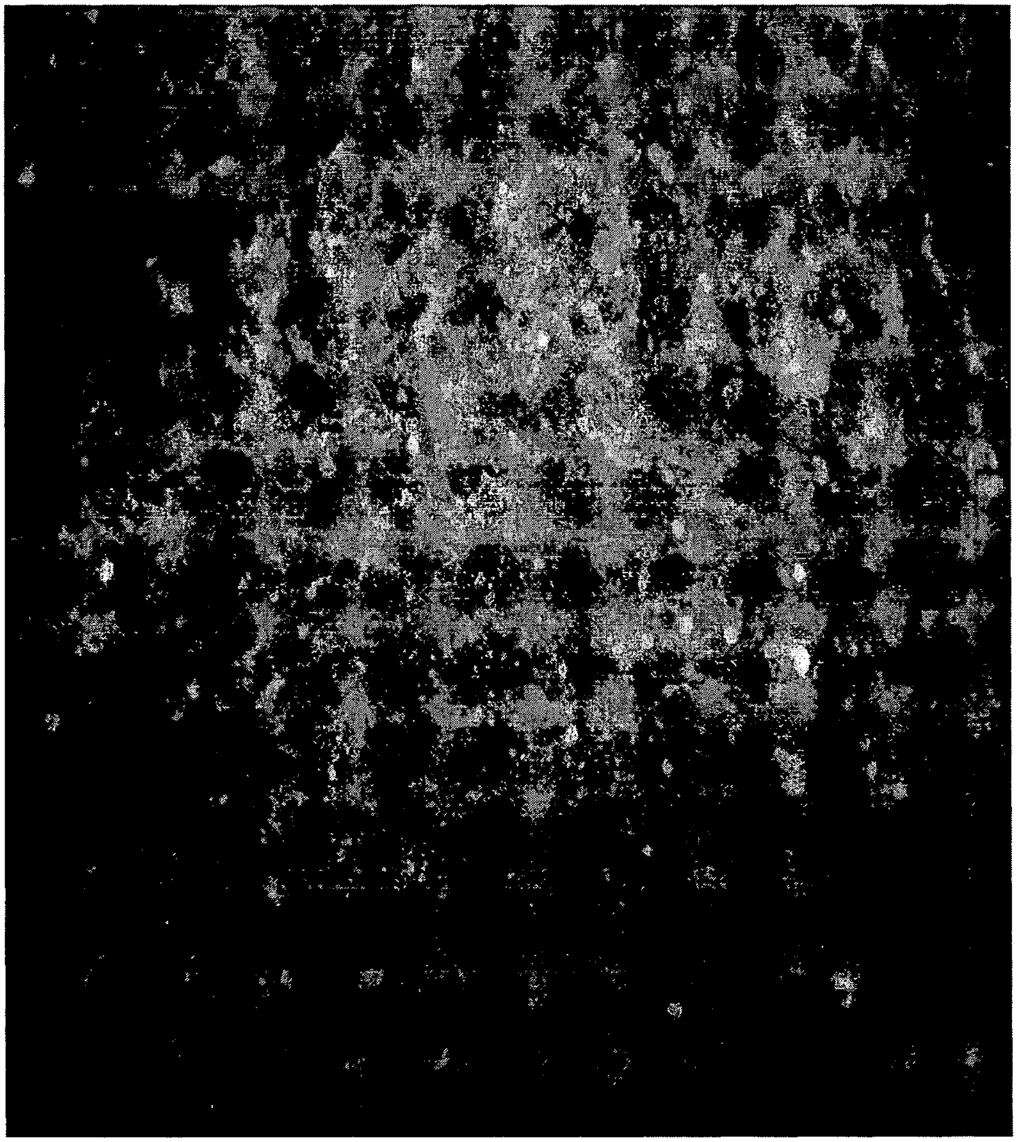
FIG. 5: Shows rabies specific fluorescence of 04PM/Chick/S.Pas.12 in Chick Embryo Culture (CEC) on day 3$^{rd}$

The original Pitman Moore strain (Wistar strain PM-HDCS, 1503-3M) is first adapted to mice via one intracerebral passage and subsequently in duck eggs by repeated passages. Subsequently, the present inventors attempted to develop an adaptation process of PM rabies virus strain to Primary Duck Embryo Fibroblast Cells, only some cells were found to be infected (FIG. 1). Over several passages, the infectivity was not increased to the satisfactory extent.

It is known, for e.g. in U.S. Pat. No. 4,115,195, that a sufficiently high virus titer is a pre-requisite for an effective rabies vaccine Hence, the inventors changed their focus to give passages of the virus into Chick Embryo Fibroblast cell culture. After several experiments for infectivity and adaptation, in chick embryo cells, successful results of virus titration were obtained (FIGS. 2 to 5).

The original "Wistar strain PM-HDCS, 1503-3M" adapted to duck embryo is herein referred to as "Master Seed DE 42/74 Pas. 12 12.11.1974" which is a master seed for production of PDEV vaccine. This "Master Seed DE 42/74 Pas. 12 12.11.1974" rabies virus is adapted and propagated initially in duck embryo cells then to Primary Chick Embryo Fibroblast Cell Cultures to produce cell culture PCEC Vaccine (PCECV$^{PM}$) for rabies according to the present invention.

Initially, the inventors attempted to adapt the "Master Seed DE 42/74 Pas. 12 12.11.1974" virus to Primary Duck Embryo Fibroblast Cells by repeated passages. But, since Primary Duck Embryo Fibroblast cells are not a 'natural' host for the PM rabies virus, the inventors could not get any infection in the initial experiments, and further optimizations only resulted in very little infection in subsequent experiments. Hence, the process was significantly modified and the passaging in Primary Duck Embryo Fibroblast cells was shifted to passaging in Primary Chick Embryo Fibroblast cells under suitable medium and culture parameters. Such passaging of PM strain of rabies virus into Primary Chick Embryo Fibroblast cells is a unique and not a routine substitution which is neither reported in the art nor can be extrapolated by a person skilled in the art as routine, since these cells are also not a 'natural' host to the PM strain of Rabies virus.

In the present invention, the "Master Seed virus DE 42/74 Pas.12 12.11.1974" was adapted to Primary Duck Embryo Fibroblast Cells, and then to Primary Chick Embryo Fibroblast Cells by repeated passages as described below:

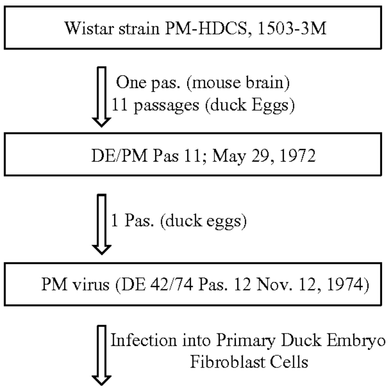

-continued

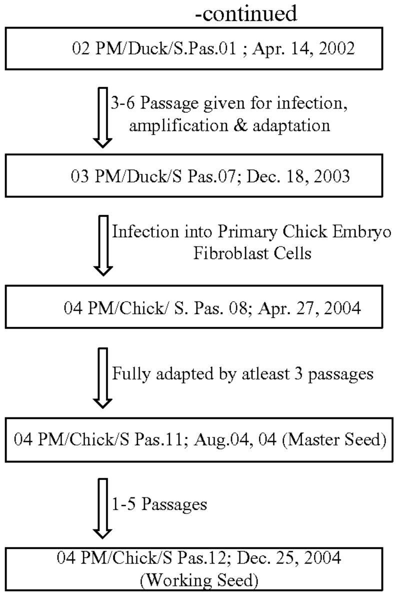

The nomenclature for the various strains obtained during passaging are in the following general format:

"year of preparation (e.g. '04' for 2004)/Pitman Moore strain (PM)/substrate in which passaging took place (duck or chick)/serial passage number/date of culture"

The adapted Pitman Moore strain which is used as a master seed or working seed is obtained by infecting PM virus (DE 42/74 Pas. 12 12.11.1974) to Primary Duck Embryo Fibroblast Cells and 7 passages were performed at temperature at 33-36° C. in order to adapt the strain in the Primary Duck Embryo Fibroblast Cells and obtained "03 PM/Duck/S Pas.07 18.12.03". The "03 PM/Duck/S Pas.07 18.12.03" strain was further infected in to Primary Chick Embryo Fibroblast Cells by at least 4 passages to obtain the master seed "04 PM/Chick/S Pas.11 04.08.04". One can give 1-5 passages from Master seed to prepare the working seed for commercial vaccine production. One Example of working seed lot prepared according to the above process was named as "04 PM/Chick/S Pas.12 25.12.04".

The virus obtained from the Master seed "04 PM/Chick/S Pas.11 04.08.04" has a peak titer of at least $10^{6.5}$ $TCID_{50}$% per ml.

The virus titer was in increasing log at successive passages in chick embryo cell, suggesting that the virus has stable phenotypic character.

At every stage of passage, infectivity was checked by staining culture with Ab tagged-FITC conjugate using fluorescence microscopy. After getting optimum and reproducible conditions for infectivity and culture, the results were confirmed primarily by Fluorescence Microscopy and then by several in-vitro as well as in-vivo tests as described in various Pharmacopoeia.

The adaptation of the virus is preferably carried out using PET TC roller bottles or multi layered TC flasks.

For proper adaptation, several medium and their combinations of ingredients were employed in described below with the help of Example 1. The present invention is further illustrated by the following non-limiting examples which represent one of the preferred mode of carrying out the invention. It will be appreciated that several non-inventive modifications, which are within the scope of a person skilled in the art are possible which are considered to be within the scope of the present invention.

Example 1

Selection of Medium for Virus Adaptation and Process Optimization

Following media were chosen for virus adaptation and process parameters optimization.

Production Culture Medium 1 (PCM 1)
Production Culture Medium 2 (PCM 2)
Production Culture Medium (PCM)

The above mentioned medium comprises below ingredients:

| MEDIUM COMPOSITION | PCM 1 Mg/L | PCM 2 Mg/L | PCM Mg/L |
|---|---|---|---|
| INORGANIC SALTS | | | |
| Calcium chloride anhydrous | 200 | 200 | 175-225 |
| Ferric (III)-Nitrate. 9H2O | 0.1 | | 0.02-0.07 |
| Magnesium sulfate anhydrous | 97.7 | 97.7 | 72.7-122.7 |
| Potassium chloride | 400 | 400 | 375-425 |
| Sodium chloride | 6400 | — | 3175-3225 |
| Sodium Dihydrogen phosphate.H2O | 125 | 140 | 107.5-157.5 |
| Sodium hydrogen Carbonate | 3700 | 2200 | 2925-2975 |
| VITAMINS | | | |
| D-calcium pantothenate | 4 | 1 | 0.5-5.0 |
| Choline chloride | 4 | 1 | 0.5-5.0 |
| Folic acid | 4 | 1 | 0.5-5.0 |
| Myo-Inositol | 7.2 | 2 | 0.6-8.6 |
| Nicotinamide | 4 | 1 | 0.5-5.0 |
| Pyridoxal HCl | 4 | 1 | 0.5-5.0 |
| Riboflavin | 0.4 | 0.1 | 0.01-0.5 |
| Thiamine HCl | 4 | 1 | 0.5-5.0 |
| AMINO ACIDS | | | |
| L-arginine HCl | 84 | 126 | 80-130 |
| L-cystine | 48 | 24 | 5-30 |
| L-glutamine | 584 | 292 | 413-463 |
| Glycine | 30 | — | 20-40 |
| L-histidine HCl. H2O | 42 | 42 | 17-67 |
| L-isoleucine | 105 | 52 | 53.5-103.5 |
| L-leucine | 105 | 52 | 53.5-103.5 |
| L-lysine HCl | 146 | 72.5 | 84.25-134.25 |
| L-methionine | 30 | 15 | 2.5-42.5 |
| L-phenylalanine | 66 | 32 | 24-74 |
| L-serine | 42 | — | 16-26 |
| L-threonine | 95 | 48 | 46.5-96.5 |
| L-tryptophan | 16 | 10 | 10-30 |
| L-tyrosine | 72 | 36 | 29-79 |
| L-valine | 94 | 46 | 45-95 |
| OTHER | | | |
| D-Glucose anhydrous | 4500 | 1000 | 2725-2775 |
| Phenol red | 15 | 11 | 10-30 |
| Sodium pyruvate | 110 | — | 30-80 |

The above media were further supplemented with human serum albumin, hydrolyzed gelatin, sodium bicarbonate and antibiotics solution at suitable concentrations.

Following experiments were carried out using different mediums and their effectiveness were compared for formation of cell monolayer and degree of virus infection.

9-11 days old embryos were taken and trypsinized 10-10-20 minutes steps. The cells were centrifuged to remove trypsin and re-suspended equally in PCM 1, PCM 2 and PCM. Cell counts were adjusted to approx. $1.7\times10^6$ cells per ml in all the three medium in different experiments. The virus "03 PM/Duck/S. Pas. 07" virus at 1:1200 dilution were used in all experiments. Adsorption time was 90 minutes for every experiments. The infected cells were seeded in Greiner TC flasks and PET Roller bottles. Representative infected cells from the TC flask/roller bottles were also seeded in 24 well TC plates. The TC flask & Roller bottles were incubated at 34° C.±1° C. for 5 days. The 24 well plate was incubated in 3% $CO_2$ environment at 34° C.±1° C. and was stained with FITC conjugate on $3^{rd}$ day to check degree of virus infection which was rated by Rabies specific fluorescence as good (+), very good (++), excellent (+++) or extraordinary (++++).

On day $4^{th}$ or $5^{th}$, cell supernatant was harvested from each set of experiment as first harvest and replenished with fresh respective culture medium. After further incubation, On day $2^{nd}$, $3^{rd}$ or $4^{th}$ from the first harvest, second harvest were taken from each set. The first harvest and second harvest were tested for virus titration and sterility.

It was found that:

In 24 well plate, cell seeded PCM 1 and PCM 2 showed poor to good infection while cell seeded in PCM showed excellent to extraordinary infection, evaluated by rabies specific immunofluorescence.

TC flask/roller bottles seeded with PCM had shown good titers compared to PCM 1 and PCM 2 alone. Titer values, $10^{5.6}$, $10^{5.8}$ and $10^{7.7}$ $TCID_{50\%}$ are found in PCM 1, PCM 2 and "PCM" respectively.

From the above results in various experiments, the medium PCM was chosen for adaptation in Primary chicken embryo fibroblast cells and subsequent vaccine preparation which was further optimized by various process parameters which are within the scope of persons skilled in the art and by further selection of suitable TC roller bottle.

General Cell and Culture Procedure Used for Preparing the Master Seed, Working Seed and Rabies Vaccine Production:

The chicken eggs were incubated for 8-11 days at a temperature 35° C.-37° C. with 70-90% RH. After incubation, the eggs were candled for live and healthy embryos. After candling, the embryos were removed from each egg under aseptic conditions then the heads and bodies were separated by pulling method. The heads were then immediately discarded while the body part of embryos were pooled in a bottle, washed three to four times with sterile PBS and trypsinized with trypsin pre-warmed at 35±2° C. for 10-40 minutes.

Trypsinized cell suspension was filtered through a nylon muslin cloth followed by centrifugation at 1000 to 1500 rpm for 10 to 15 min in refrigerated centrifuge. The cell pellet is suspended in fresh growth medium, mixed well and again this cell suspension was centrifuged in the same manner. The cell pellet was suspended in fresh growth medium and mixed thoroughly. The cell suspension was transferred into a sterile glass bottle containing above said culture medium and stirred for 5-10 minutes at 35±2° C. The final cell counts were adjusted in the range of $1.4\text{-}2.2\times10^6$/ml using culture medium in 20 L glass bottle.

The cell suspension was inoculated with pre-determined optimum master or working seed virus dilution and incubated under slow stirring at 35±2° C. for 90-120 minutes for adsorption of virus to cells. At the end of adsorption, infected virus suspension were distributed either in PET TC roller bottles (300±50 ml per TC Roller bottle) or in multilayer TC flask such as cell factories or cell stacks (3000±500 ml) or combination of both. They were then incubated at 34.5±0.5° C. for 4 to 6 days. On day $4^{th}$ or $5^{th}$, cell supernatant was harvested as first harvest and replenished with fresh culture medium. After further incubation, second was taken on day $7^{th}$ or $8^{th}$. Third harvest is optional. Various virus harvests were stored at 2°-8° C. Multiple harvest make the invention cost effective by getting more harvest with good titers The pooled virus harvest were purified and concentrated by ultracentrifugation in a sucrose density gradient zonal centrifuge at 35000 rpm. Banding of the rabies virus takes place best between a sucrose concentration of approximately 35-40% and the sucrose gradient/bands having active live rabies Virus were collected as product fractions. The product fraction virus concentrates from various pooled harvests were stored below −60° C. until results of various test like In-vitro Ag assay, sterility test and Bacterial endotoxin tests were clear.

The present invention also provides a method of inactivating PM virus to destroy its infectivity while preserving its antigenicity. The concentrates were thawed at 37° C. and cooled at 4±2° C. The concentrates were diluted by vaccine stabilizer to achieve appropriate antigen content of 8.5 IU/ml and sample were withdrawn for In-vitro Ag assay like ABT, ELISA and SRD test. The pH of the blended bulk was measured and adjusted to 8.0±1 with 10% w/v pre-sterilized NaOH solution. Then effective quantity of Betapropiolactone diluted 1:100 in PBS was slowly added into the blended bulk so as to reach a final concentration of 1:4000 (0.025%) and the content of vessel was transferred into another pre-sterilized inactivation vessel. The incubation with Betapropiolactone was performed at 2° to 6° C. under constant stirring. At least 48 hours were required to fully inactivate viral infectivity without losing viral antigenicity. The inactivation process of PM virus at 2° C. 6° C. was preferably chosen for simplicity in large scale culture.

Finally the inactivated bulk was Stored at 5°±3° C. until further processing under continuous stirring. The inactivated bulk was diluted with suitable stabilizer solution to adjust antigenic value of at least 5 IU/ml. During the blending process, the blended bulk was maintained at 5°±3° C. under stirring. The blended vaccine was stirred for 30 minutes prior to filling. Lyophilisation was done by standard methods known in the art. Vaccine stabilizer used contains sucrose, hydrolyzed gelatine, human albumin and sodium salts. The vaccine is prepared as a freeze-dried formulation to be reconstituted with sterile water for injection.

Figure 6:
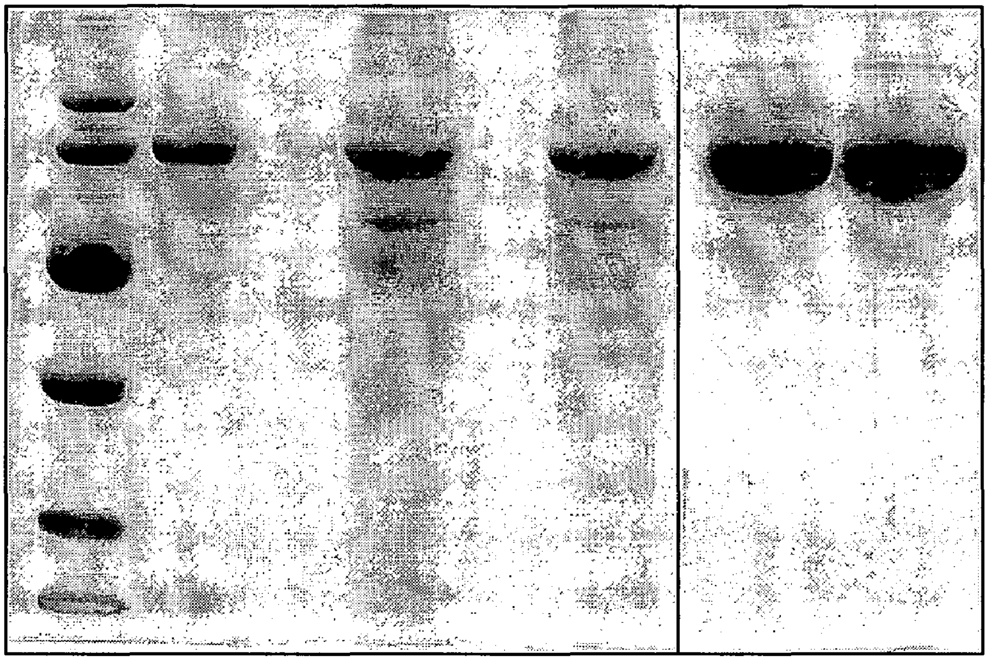
FIG. 6: Comparison of Experimental Vaccine of the present invention with various Marketed rabies Vaccines.

The efficacy and immunogenicity of vaccine prepared using chick fibroblast cells is same as International Reference Vaccine (WHO $5^{th}$ IRM) which has been evaluated by various animal safety, efficacy and seroconversion studied. Further, the end product purity is verified and compared by SDS page which is similar to other marketed products (FIG. 6). The product is also very stable when stored at 2° to 8° C. it also retains potency and other critical parameters when exposure at accelerated and stressed temperatures as per ICH guidelines for stability of Biotechnological and biological materials.

Example 2

Adaptation of Pitman Moore Rabies Virus Strain to Primary Duck Embryo Fibroblast Cells and Successive Adaptation of the Virus Obtained Therein to Primary Chick Embryo Fibroblast Cells (A) The original Pitman Moore rabies virus strain (Wistar strain PM-HDCS, 1503-3M) was first adapted by 1 cerebral passage in Swiss Albino Mice followed by 12 passages in embryonated Duck eggs, and the virus obtained was named as DE 42/74 Pas. 12 12.11.1974. The present invention uses this virus for further adaptation to primary duck embryo fibroblast cells and subsequently chick embryo fibroblast cells.

The experiment was carried out by using 11-12 days old SPF duck eggs. The cell count was set at $1.8\times10^6$ cell/ml as per techniques known, cell suspension was prepared by using Production Culture Medium 1 (PCM 1, described above) with supplement of 1.5% human albumin. 5 ml frozen aliquot of above named virus “DE 42/74 Pas. 12 12.11.1974” was thawed at 37° C. and diluted in cell culture stabilizer, and was used for infecting the duck embryo cell suspension. The infected cell suspension was filled into TC PET roller bottles and incubated at 34° C. On day five after the infection, the harvest was collected from the roller bottles and tested for virus titer in mice and for absence of contaminants like bacteria and fungi. These harvested virus was named as “02 PM/DUCK/S Pas.01”

Like wise six such passages were further done in duck embryo cell culture and after each passage, harvest of approximately 7.0 liters. After each passage the harvest was collected and tested for virus titer in mice and for absence of contaminants like bacteria and fungi. The harvest from each passage was further distributed in 5 ml aliquots. They were named as follows.

| Culture date. | No of eggs | Approximate Vol. of harvest | Ex. 1: Nomenclature |
|---|---|---|---|
| 14.04.02 | 180 | 07 ltrs | 02 PM/Duck/S. Pas. 01 |
| 27.07.02 | 180 | 07 ltrs | 02 PM/Duck/S. Pas. 02 |
| 30.11.02 | 180 | 07 ltrs | 02 PM/Duck/S. Pas. 03 |
| 11.01.03 | 180 | 07 ltrs | 03 PM/Duck/S. Pas. 04 |
| 04.10.03 | 180 | 07 ltrs | 03 PM/Duck/S. Pas. 05 |
| 17.11.03 | 180 | 07 ltrs | 03 PM/Duck/S. Pas. 06 |
| 18.12.03 | 180 | 07 ltrs | 03 PM/Duck/S. Pas. 07 |

During the above experiments, after initial passage, only few cells were found infected and showed rabies specific fluorescence. The infectivity of virus gradually and significantly increased from the fourth passage onwards. This can be shown as in the below chart:

DE 42/74 Pas. 12 Nov. 12, 1974

1 passage in Duck embryo cell culture

02 PM / Duck / S. Pas 01 Apr. 14, 2002

1 passage in Duck embryo cell culture

02 PM / Duck / S. Pas 02 Jul. 27, 2002

1 passage in Duck embryo cell culture

02 PM / Duck / S. Pas 03 Nov. 30, 2002

1 passage in Duck embryo cell culture

02 PM / Duck / S. Pas 04 Jan. 11, 2003 ($10^{2.4}$ $LD_{50\%}$/ml)

1 passage in Duck embryo cell culture

02 PM / Duck / S. Pas 05 Oct. 04, 2003 ($10^{3.5}$ $LD_{50\%}$/ml)

1 passage in Duck embryo cell culture

-continued

02 PM / Duck / S. Pas 06 Nov. 17, 2003 ($10^{3.8}$ $LD_{50\%}$/ml)

1 passage in Duck embryo cell culture

03 PM / Duck / S. Pas 07 Feb. 18, 2003 ($10^{5.0}$ $LD_{50\%}$/ml)

After seventh passage infectivity was almost constant. Several alternatives were tried with very little success. Surprisingly, when the virus “03 PM/Duck/S. Pas 07 18.02.03” was infected into chick embryo fibroblast cells, the infectivity increased significantly. Based on this findings, the virus strain was further passaged in chick embryo fibroblast cells in order to achieve required infectivity and virus titer as follows.

(B) Approximately 9-11 days old (180 embryos) fertilized SPF chicken eggs was used for the process and the head part was separated from the body part, the body part only was processed, while the head part was discarded. The pooled body parts were given repeated phosphate buffered saline wash and subsequently the embryos were trypsinized using trypsin solution. Cell suspension was prepared in PCM, the cell count was set at $1.6\times10^6$ cells/ml. The 5 ml frozen aliquot of “03 PM/Duck/S. Pas. 07” was thawed at 37° C. and diluted in stabilizer. This was used for infecting the chick embryo cell suspension. This infected cell suspension was incubated at 37° C. for 1.5 hrs with slow stirring. The infected cells were distributed into roller bottle as well as in multilayered TC flasks, and incubated at 34° C. On day five of the infection, the harvest was collected from the roller bottles and multilayered TC flasks, approximately 7 ltrs of harvest was collected and was distributed in suitable aliquots and from these aliquots few aliquots of 5 ml were used for testing virus titer in mice and for absence of contaminants like bacteria and fungi.

These virus harvest was given nomenclature as “04 PM/Chick/S. pas 0.8”

| Culture date | No of eggs | Approximate Vol. of harvest | Nomenclature |
|---|---|---|---|
| 27.04.04 | 180 | 07 ltrs | 04 PM/Chick/S. Pas. 08 |
| 11.05.04 | 180 | 07 ltrs | 04 PM/Chick/S. Pas. 09 |
| 16.07.04 | 180 | 07 ltrs | 04 PM/Chick/S. Pas. 10 |
| 04.08.04 | 180 | 07 ltrs | 04 PM/Chick/S. Pas. 11 |
| 25.12.04 | 180 | 07 ltrs | 04 PM/Chick/S. Pas. 12 |

Subsequently, 3 further successive passages of the virus were given in chicken fibroblast cells, aliquots from each harvest were collected and distributed in 5 ml aliquots and were given the nomenclature as mentioned above. All the passage were tested for virus titer and absence of bacteria and fungi.

Based on data obtained, the virus obtained after the $4^{th}$ passage named “04 PM/Chick/S Pas. 11 04.08.04” has $10^{7.7}$ $LD_{50\%}$ virus titer per ml which was herein considered as Master Seed Virus. This virus was given 1 further passage to produce the Working Seed Virus “04 PM/Chick/S Pas. 12 25.12.04”

Example 3

Preparation of Vaccine from the Working Seed

The seed Virus “04 PM/Chick/S Pas. 12 25.12.04” was infected in chicken fibroblast cell by a process similar to that described in step 1(b) above, and first harvest was obtained on or after 4 days and the second harvest was obtained after 2-3 days of the first harvest. The pooled virus harvest were purified and concentrated by ultracentrifugation by a sucrose density gradient zonal centrifuge at 35000 rpm. Banding of the rabies virus was carried out at approx. 35-40% of sucrose concentration and the active live rabies Virus were collected as product fractions. The virus concentrates from various pooled harvests were stored below—60° C. until results of various test like in-vitro Ag assay, sterility test and bacterial endotoxin tests were clear.

The concentrates were thawed at 37° C. and cooled at 4±2° C. The concentrates were diluted by vaccine stabilizer to achieve appropriate antigen content of 8.5 IU/ml and sample were withdrawn for In-vitro Ag assay like ABT, ELISA and SRD test. The pH of the blended bulk was measured and adjusted to 8.0±1 with 10% w/v pre-sterilized NaOH solution. The blended bulk was then inactivated by addition of suitable concentration of Betapropiolactone, by known techniques.

Finally the inactivated bulk was stored at 5°±3° C. under continuous stirring and was diluted with suitable stabilizer solution to adjust antigenic value at ≧5 IU/ml and blended bulk was maintained at 5°±3° C. under stirring for 30 minutes. The blended bulk was filled in vials and using suitable stabilizer composition comprising sucrose, hydrolyzed gelatine, human albumin and sodium salts. The vaccine is made available as a freeze-dried formulation to be reconstituted with sterile water for injection prior to use.

The immunogenicity and potency of the vaccine were tested as follows:

Example 4

NIH Potency Test in Mice

The NIH Potency test in mice is carried out as per Laboratory Techniques in Rabies, 4th ED. WHO '1996 and Indian Pharmacopoeia.

The potency of rabies vaccine is determined by comparing the dose of the experimental vaccine necessary to protect mice against a lethal intra-cerebral dose of rabies virus with the corresponding dose of reference vaccine (WHO $5^{th}$ IRM, 16.0 IU per Ampoule) necessary to give the same protection.

Swiss Albino Mice weighing approximately 12-15 grams were used.

| No. of Mice Required | |
|---|---|
| Standard Vaccine | 64 (16 × 4 Dilutions) |
| Test Vaccine | 64 (16 × 4 Dilutions) |
| Virus Titration | (10 × 4 Dilutions) |

One dose of International Reference vaccine was reconstituted in 2.0 ml of water for injection; and 0.5 ml of it was mixed thoroughly with 12 ml of Phosphate Buffer Saline (PBS) to make 25 fold dilution.

One dose from at-least each shelves of freeze dried lots of the experimental vaccine of the invention were reconstituted separately in 1.0 ml of water for injection, and then pooled together. Take out 0.5 ml which was mixed thoroughly with 12 ml of PBS thereby making a 25 fold dilution.

Subsequently, three five fold dilutions of both International Standard and Experimental vaccines were prepared in PBS (pH 7.4). The range of dilutions were so selected that the middle dilution contained enough vaccine to protect 50% of total number of mice taken for the study, with the challenge dose of virus of 10-50 $LD_{50}$. The dilution range of 1:25, 1:125, 1:625, 1:3125 worked well for both, standard as well as experimental vaccine.

During first immunization sixteen mice (8 Males+8 Females) were injected with 0.5 ml of each dilution, by intraperitoneal route and second immunization was done after seven days from the day of first immunization, repeating the steps as that of first vaccination.

Virus Challenge (Infection) to the Immunized Mice

Fourteen days after $1^{St}$ immunization, all mice were infected with Brain Suspension of Challenge Virus Standard (CVS); dose of which adjusted between 10-50 $LD_{50}$.

Observation of Experimental Animals

Infected mice are observed for 14 days. Mice deaths are noted after fifth day of infection.

Calculation of Potency

The potency was calculated by REED and MUENCH method. It was found that:

The $ED_{50}$ values of the Test as well as Standard Vaccines were between the highest and the lowest dose administered to the experimental animals.

The titration of the challenge suspension showed that 0.03 ml. of it contained between 10 to 50 $LD_{50}$ and all the animals should die which received the suspension of this strength.

The confidence limits of the level of significance (p=0.95) were not less than 25% and not more than 400% of the calculated potency.

The final result is tabulated below.

| Lot No. | Test | Potency (IU/dose) | Confidence Limit (95%) | Challenge Virus Dose | Mean Potency (IU/dose) |
|---|---|---|---|---|---|
| 1 | I | 5.42 | 2.667-10.928 | 26.30 | 5.43 |
| | II | 5.50 | 2.541-11.928 | 26.92 | |

From the above experiment, it can be concluded that the mean potency of the experimental vaccine is 5.43 IU/dose. The 95% confidence limit of each test is between 25-400% of the calculated potency. The challenge virus dose (CVD) used in each test was between 10-50 $LD_{50}$. $ED_{50}$ of standard and test vaccine in each test was between the highest and lowest dilution. Hence it can be concluded that the vaccine is immunoprotected and NIH potency value is well above the minimum requirement of 2.5 IU/dose.

Example 5

Seroconversion and Challenge Study in Rabbits

From the positive results obtained in mice in terms of seroconversion/challenge study, a combined study was designed to ascertain seroconversion and protection in rabbits. New Zealand White Rabbits having weight within 1.5-2.5 Kgs were used, 5 males & 5 females rabbits were taken per group, WHO $5^{th}$ IRM, reconstituted in 2 ml of Sterile Water for Injections to get 8 IU/ml was used as Reference vaccine. The Experimental vaccine of the present invention was reconstituted in 1 ml of Sterile Water for Injection.

All the rabbits in each group were injected intra-muscularly with 0.5 ml of respective vaccines on day 0 and on day 7 and were observed for 14 days. On day 14, 2 ml of blood was collected aseptically from Marginal Ear vein of each rabbit and blood was allowed to clot by incubation at 37° C. for 1 hour. The blood samples were centrifuged at 1,500 rpm/10 mins for serum separation and serum was collected aseptically in pre-sterilized tubes/cryovials. The samples were heat-inactivated at 56° C. for 30 minutes and stored below −60° C. for further titer determination.

The antibody titer in each sample was determined by Rapid Fluorescent Focus Inhibition Test (FRRIT) and Mouse Neutralization Test. Subsequently, all rabbits were challenged intra-cerebrally with 30MLD$_{50}$/0.3 ml of Challenge Virus Standard (CVS-27) under Intravenous anaesthesia (Thiopentone sodium). The rabbits were observed for 14 days for Rabies specific symptoms and mortality. The mortality upto day 5$^{th}$ was considered non-specific death.

Observation:

It was observed that none of the rabbit in any group exhibited Rabies specific symptoms or died. The test vaccine was similar in immunogenicity with respect to reference vaccine as can be inferred from the table.

Sero Conversion in Rabbit

Group I: Reference Rabies Vaccine (WHO 5$^{th}$ IRM)

| | | Antibody titer (IU/ml) | |
|---|---|---|---|
| Rabbit No. | Sex | RFFIT | MNT |
| 1 | Male | 4.65 | 9.6 |
| 2 | Male | 7.39 | 11.5 |
| 3 | Male | 8.10 | 10.0 |
| 4 | Male | 6.92 | 11.5 |
| 5 | Male | 8.10 | 8.91 |
| 6 | Female | 5.86 | 11.0 |
| 7 | Female | 11.73 | 10.0 |
| 8 | Female | 12.53 | 8.91 |
| 9 | Female | 8.10 | 6.0 |
| 10 | Female | 11.73 | 13.2 |
| Mean | — | 8.51 | 10.06 |
| S.D. | — | 2.65 | 1.95 |

Group II: Experimental Test Vaccine (PCEC Rabies Vaccine)

| | | Antibody titer (IU/ml) | |
|---|---|---|---|
| Rabbit No. | Sex | RFFIT | MNT |
| 1 | Male | 11.73 | 9.12 |
| 2 | Male | 8.10 | 9.14 |
| 3 | Male | 5.86 | 8.91 |
| 4 | Male | 6.92 | 11.48 |
| 5 | Male | 7.39 | 12.88 |
| 6 | Female | 8.10 | 13.80 |
| 7 | Female | 4.65 | 13.20 |
| 8 | Female | 6.92 | 11.48 |
| 9 | Female | 12.53 | 12.0 |
| 10 | Female | 8.10 | 6.70 |
| Mean | — | 8.2 | 10.87 |
| S.D. | — | 3.2 | 2.29 |

Inference:

From the antibody titer obtained for experimental test vaccine (Mean: 8.2 & 10.87 by RFFIT & MNT respectively) as well as reference vaccine (Mean: 8.51 & 10.06 by RFFIT & MNT respectively), it was concluded that the Experimental vaccine of the present invention is equally immunogenic as the reference vaccine.

Therefore, one can conclude from the results obtained after challenge, that the PCEC vaccine (Experimental vaccine) prepared according to the process of the present invention is equally protective as the reference standard in terms of immunogenicity and potency.

Example 6

Comparison of Experimental Vaccine of the Present Invention with Various Marketed Rabies Vaccines The SDS page analysis was carried out to check and compare the protein banding of the Experimental rabies vaccine with those of other marketed products using known markers.

From the study it was observed (FIG. 6) that the virus concentrate of the present invention when formulated like other marketed rabies vaccines showed identical protein bands.

In the FIG. 6,

Lane 1: Low molecular weight marker;

Lane 2: API of the present invention;

Lane 3: API, of the present invention formulated like other marketed PCEC rabies vaccine;

Lane 4: Marketed PCEC rabies vaccine;

Lane 5: Vero cell line based marketed rabies vaccine;

Lane 6: API of the present invention formulated like other marketed Vero rabies vaccine.

We claim:

1. A process of adaptation of Pitman Moore strain of rabies virus to primary chick fibroblast cells for the production of rabies vaccine comprising the steps of a) adapting the Pitman Moore rabies virus strain in a primary duck embryo fibroblast cell culture by suitable number of passages in a suitable medium; and b) subsequently, adapting the viruses in a primary chick fibroblast cell culture by suitable number of passages in a suitable medium, wherein the Pitman Moore Strain is obtained by passaging Wistar strain "PM-HDCS, 1503-3M," in duck eggs.

2. The adaptation process according to claim 1 step (a) wherein the Pitman Moore rabies virus strain is first adapted to primary duck embryo fibroblast cell culture by at least 7 passages.

3. The adaptation process according to claim 1 step (b) wherein the Pitman Moore rabies virus strain is adapted to primary chick embryo fibroblast cell culture by at least 4 passages.

4. The process of claim 1, wherein medium used is production culture medium (PCM) which comprises

| Ingredient | Concentration (Mg/L) |
|---|---|
| Calcium chloride anhydrous | 175-225 |
| Ferric (III)-Nitrate. 9H2O | 0.02-0.07 |
| Magnesium sulfate anhydrous | 72.7-122.7 |
| Potassium chloride | 375-425 |
| Sodium chloride | 3175-3225 |
| Sodium Dihydrogen phosphate. H2O | 107.5-157.5 |
| Sodium hydrogen Carbonate | 2925-2975 |
| D-calcium pantothenate | 0.5-5.0 |
| Choline chloride | 0.5-5.0 |
| Folic acid | 0.5-5.0 |
| Myo-Inositol | 0.6-8.6 |
| Nicotinamide | 0.5-5.0 |
| Pyridoxal HCl | 0.5-5.0 |
| Riboflavin | 0.01-0.5 |
| Thiamine HCl | 0.5-5.0 |
| L-arginine HCl | 80-130 |
| L-cystine | 5-30 |

-continued

| Ingredient | Concentration (Mg/L) |
|---|---|
| L-glutamine | 413-463 |
| Glycine | 20-40 |
| L-histidine HCl. H2O | 17-67 |
| L-isoleucine | 53.5-103.5 |
| L-leucine | 53.5-103.5 |
| L-lysine HCl | 84.25-134.25 |
| L-methionine | 2.5-42.5 |
| L-phenylalanine | 24-74 |
| L-serine | 16-26 |
| L-threonine | 46.5-96.5 |
| L-tryptophan | 10-30 |
| L-tyrosine | 29-79 |
| L-valine | 45-95 |
| OTHER | |
| D-Glucose anhydrous | 2725-2775 |
| Phenol red | 10-30 |
| Sodium pyruvate | 30-80. |

5. The process as claimed in claim 4, wherein the medium further comprises human serum albumin, hydrolysed gelatin, sodium bicarbonate and antibiotics.

6. The process according to claim 1, wherein the duck embryo fibroblast cell culture has maintained cell count in the range of $1.4-2.2\times10^6$ cells per ml.

7. The process according to claim 1, wherein the adaptation is carried out in a Polyethylene Terephthalate (PET) Tissue Culture treated (TC) roller bottle or multilayered TC flask.

8. The process of preparation of rabies vaccine from the Pitman Moore strain adapted in primary chick embryo fibroblast cell by the process as claimed in claim 1.

9. The process according to claim 1, wherein the primary chick fibroblast cell culture has maintained cell count in the range of $1.4-2.2\times10^6$ cells per ml.

* * * * *